United States Patent
Bhatnagar et al.

(10) Patent No.: US 6,489,165 B2
(45) Date of Patent: *Dec. 3, 2002

(54) CHONDROCYTE-LIKE CELLS USEFUL FOR TISSUE ENGINEERING AND METHODS

(75) Inventors: Rajendra S. Bhatnagar, Burlingame, CA (US); Steven B. Nicoll, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/760,629

(22) Filed: Jan. 16, 2001

(65) Prior Publication Data

US 2001/0005592 A1 Jun. 28, 2001

Related U.S. Application Data

(63) Continuation of application No. 09/204,824, filed on Dec. 3, 1998, now Pat. No. 6,197,586.
(60) Provisional application No. 60/069,582, filed on Dec. 12, 1997.

(51) Int. Cl.$^7$ .................................................. C12N 5/00
(52) U.S. Cl. ...................... 435/395; 435/377; 435/383; 435/404; 424/93.21; 623/4
(58) Field of Search ................................ 435/395, 377, 435/383, 404; 424/93.21; 623/4

(56) References Cited

U.S. PATENT DOCUMENTS

| | | | |
|---|---|---|---|
| 4,642,120 A | 2/1987 | Nevo et al. | |
| 5,368,858 A | 11/1994 | Hunziker | |
| 5,632,745 A | 5/1997 | Schwartz | |
| 5,786,217 A | 7/1998 | Tubo et al. | |
| 5,866,415 A | 2/1999 | Villeneuve | |
| 5,902,741 A | 5/1999 | Purchio et al. | |
| 6,197,586 B1 * | 3/2001 | Bhatnagar et al. | |

OTHER PUBLICATIONS

Alberts et al. (1989). "Fibroblasts and their transformations: The connective–tissue cell family" *Molecular Biology of the Cell*, (2$^{nd}$ Ed.), pp. 986–989.

Buckwalter et al. (1997). "Articular cartilage, Part I: Tissue design and chondrocyte–matrix interactions" *Journal of Bone and Joint Surgery*, vol. 79–A(4): 600–611.

Buckwalter et al. (1997). "Articular cartilage, Part II: Degeneration and osteoarthrosis, repair, regeneration, and transplantation" *Journal of Bone and Joint Surgery*, vol. 79–A(4): 600–611.

Jackson et al. (1996). "Chondrocyte transplantation" *Arthroscopy: The Journal of Arthroscopic and Related Surgery*, vol. 12(6): 732–738.

Kulyk et al. (1992). *J. Craniofacial Genet. Dev. Biol.*, vol. 12(2): 90–97.

Mizuno et al. (1996). "Three–dimensional composite of demineralized bone powder and collagen for in vitro analaysis of chondroinduction of human dermal fibroblasts" *Biomaterials*, vol. 17(18): 1819–1825.

Mizuno et al. (1996). "Chondroinduction of human dermal fibroblasts by demineralized bone in three–dimensional culture" *Experimental Cell Research*, vol. 227: 89–97.

Wagget et al. (1998). "Characterization of collagens and proteoglycans at the insertion of the human Achilles tendon" *Matrix Biology*, vol. 16: 457–470.

Abstract from MEDLINE of Rajpurohit et al. (1996). "Adaptation of chondrocytes to low oxygen tension: Relationship between hypoxia and cellular metabolism" *Journal of Cellular Physiology*, vol. 168(2): 424–432.

Abstract from MEDLINE of Van Noorden et al. (1995). "Ectopic mineralized cartilage formation in human undifferentiated pancreatic adenocarcinoma explants grown in nude mice" *Calcified Tissue International*, vol. 52: 145–153.

Abstract from MEDLINE of von der Mark (1979). "Cartilage cell differentiation: Review" *Clinical Orthopaedics and Related Research*, vol. 139: 185–205.

(1999). Written Opinion in related International Application No. PCT/US98/25918.

Nicoll et al. (1998) "Induction of a Chondrocyte–like Phenotype in Human Dermal Fibroblasts: Application to Cartilage Tissue Engineering." *Society for Biomaterials* (Apr. 22–26, 1998).

* cited by examiner

Primary Examiner—Leon B. Lankford, Jr.
(74) Attorney, Agent, or Firm—Bozicevic, Field and Francis LLP; Carol L. Francis

(57) ABSTRACT

Fibroblast cells are treated with a chemical inhibitor of protein kinase C such as staurosporine, in conjunction with functionally hypoxic micromass culture so as to be induced into chondrogenic differentiation. Such fibroblast-derived, chondrocyte-like cells may be seeded onto three-dimensional polymer scaffolds for use in the repair of articular cartilage lesions, and thus can obviate the need for invasive techniques to harvest autologous chondrocytes from a limited supply of existing articular cartilage, or to avoid the need for obtaining allogeneic chondrocytes from non-biocompatible donor tissues.

14 Claims, 4 Drawing Sheets

CHONDROCYTE-LIKE CELLS USEFUL FOR TISSUE ENGINEERING AND METHODS

This application is a continuation of prior application No. 09/204,824, filed Dec. 3, 1998, now U.S. Pat. No. 6,197,586, issued on Mar. 6, 2001, which claims benefit of provisional application No. 60/069,582, filed Dec. 12,1997.

FIELD OF THE INVENTION

The present invention generally relates to tissue engineering applications, and more particularly for repair of cartilage and treatment of bony defects by uses of chondrocyte-like cells prepared from fibroblasts.

BACKGROUND OF THE INVENTION

Annually, over one million procedures involving cartilage replacement are performed in the United States. Many are as a result of debilitating ailments affecting articular cartilage. Articular cartilage is a thin layer of soft connective tissue (0.5–5 mm thick) that covers the articulating surfaces of long bones in synovial joints. The principal function of articular cartilage is to redistribute applied loads and to provide a low friction-bearing surface to facilitate movement within these joints. The most common of the pathological conditions affecting articular cartilage is osteoarthritis (OA), a degenerative joint disease that afflicts between 32–38 million Americans. OA is characterized by a progressive loss of cartilage tissue due to excessive mechanical trauma or to continual loading overtime, resulting in joint pain and stiffness. Unlike other connective tissues, cartilage has a limited reparative ability because it lacks a reservoir of undifferentiated mesenchymal cells that can be recruited to a defect in aid in wound repair (whereas bone possesses marrow and periosteum-derived precursor cells on the inner and outer portions of the tissue, respectively). In addition, cartilage is an avascular tissue, and therefore, cannot rely upon the circulatory system to transport nutrients and cells to sites of damage. Thus, one approach that has been used has been to expose damaged cartilage tissue to stimuli by drilling or scraping through the cartilage into the subchondral bone to cause bleeding. However, when repair does occur, it often results in the formation of fibrocartilage which lacks the structural components and organization to withstand the mechanical demands of the natural tissue. As such, there is a need to develop effective replacement therapies for articular cartilage to restore its biological function.

Current surgical procedures to correct cartilage tissue defects involve primarily the use of autogenous or allogeneic tissue grafts. Autogenous grafts are biocompatible, but their use is limited due to a lack of tissue supply, and because of pain and morbidity which often develop at the donor site. Furthermore, the mechanical integrity of the tissue at the donor site may be compromised, rendering the remaining cartilage more susceptible to damage in the future. Allograft tissue, on the other hand, is more readily available, but the risk of disease transmission and immune responses to alloantigens present difficulties.

Recent advances in the fields of cell and molecular biology, biotechnology, and biomaterials have led to the emergence of tissue engineering, an exciting new discipline applying both engineering and life science principles to the formation of biological substrates capable of regenerating functional mammalian tissues both in vitro and iii vivo. Present attempts to engineer articular cartilage involve the isolation of primary, differentiated cells (i.e. chondrocytes) from biopsies of existing cartilage tissue and seeding these cells onto three-dimensional carrier materials. A major limitation of these techniques is that the cells are often procured from an autologous source. As such, the problem of limited donor tissue supply is not circumvented as the cellular component of the implant is harvested from host cartilage tissue. In addition, invasive surgical procedures are required to obtain the necessary quantity of cells. Alternatively, the procurement of cells from cadavers carries the inherent risk of transfer of pathogens, and the undue expense of screening for the presence of harmful pathological agents. The drawback to both of these approaches stems from the source of cellular material.

It is known that connective-tissue cells, including fibroblasts, cartilage cells, and bone cells, can undergo radical changes of character. Thus, as explained by Alberts et al., *Molecular Biology of the Cell*, (2nd Ed., 1989, pp. 987–988), a preparation of bone matrix may be implanted in the dermal layer of the skin and some of the cells there converted into cartilage cells and later others into bone cells. Cultured cartilage cells, or chondrocytes, can be converted so as to acquire characteristics of fibroblasts and stop producing type II collagen (characteristic of cartilage), but instead start producing type I collagen (characteristic of fibroblasts).

Hunziker, U.S. Pat. No. 5,368,858, issued November 29, 1994, describes matrix compositions for the treatment or repair of cartilage including a transforming growth factor associated with a delivery system contained within the matrix. The transforming growth factor is described as TGF-$\beta$ said to be capable of inducing conversion of repair cells into chondrocytes. Shorts, U.S. Pat. No. 5,632,745, issued May 27, 1997, describes a cartilage repair unit with a matrix in which "repair factors" such as fibroblast growth factor and "TGF-$\beta$" are included. Thus, a chondrogenic growth-supporting matrix is said to permit vascular invasion and cellular migration between healthy cancellous bone and the damaged articular cartilage area.

A great variety of materials said to be useful as scaffolds, or matrices, are known and proposed for cartilage implants. For example, materials such as collagen gels, poly(D,L-lactide-co-glycolide) (PLGA) fiber matrices, polyglactin fibers, calcium alginate gels, polyglycolic acid (PGA) meshes, and other polyesters such as poly-(L-lactic acid) (PLLA) and polyanhydrides are among those suggested and are in varying degrees of development and use. However, osteoinductive cells, such as improved chondrocyte-like cells for tissue engineering applications, without the problems of invasive surgery for the recipient from other regions of the body or cells without risk of disease transmission from others, remain desirable for uses such as seeding the synthetic matrices.

SUMMARY OF THE INVENTION

In one aspect of the present invention, fibroblasts are first converted to chondrocyte-like cells by treating with a combination of agents. One agent is an hypoxia mimicking agent and the second agent is a chemical inhibitor of protein kinase C (PKC). These converted chondrocyte-like cells display at least one cartilage phenotype.

Typical cartilage phenotypes are the cellular morphology, the production of cartilage matrix components, the expression of the aggrecan and type II collagen MRNA, and the down-regulation of type I collagen mRNA. Thus, the converted chondrocyte-like cells of the invention will typically show an increase in aggrecan and in type II collagen mRNA expressions and a decrease in type I collagen MRNA. Such a display of cartilage phenotype is illustrated, for example, by FIG. 5.

The initial conversion of chondrocyte-like cells is preferably where the cells are cultured in a high density micromass with conversion occurring in a period occurring from about 12 hours up to about 36 hours. The high density micromass culture is preferably achieved on a biocompatible (preferably biodegradable) scaffold. Such a scaffold assists in creating the high density micromass and can subsequently serve as a template for cartilage repair. The so-converted cells, when attached to a scaffold, can thereafter be maintained with the chondrocyte phenotype for about one to two weeks prior to implantation by maintaining them in a chemically defined, serum-free media.

The inventive cells are useful in a variety of reparative applications, including the repair of articular cartilage in synovial joints, of tracheal and esophageal cartilage, and for cosmetic purposes including modification of nasoseptal and ear cartilage. Other applications include intervertebral disc repair as an alternative to spinal fusion following disc herniation, oral and maxillofacial surgery including temporomandibular joint disc replacement, and treatment of osteochondral and bony defects.

Chondrocyte-like cells of the invention are preferably used in reparative applications by being placed in a suitable matrix in the desired site for repair. The matrix is preferably partly or entirely formed by scaffold on which the cells were preferably seeded and converted. Preferred matrices are biodegradable, and can direct cellular remodeling through mechanical influences such as fine fibers and surface treatments to enhance cell attachment and alignment.

DETAILED DESCRIPTION OF THE PREFERRED EMBODIMENT

Practice of the subject inventive method preferably begins with fibroblast cells. For convenience, human dermal fibroblasts are particularly preferred, although any fibroblast population should be acceptable (i.e. tendon, ligament, synovial fibroblasts). Human dermal fibroblasts are preferred because they can be harvested non-invasively by punch biopsy from as little as a 3-mm diameter circular tissue specimen. Conversion of autologous dermal fibroblasts would be the preferred approach for patients who have scheduled tissue repair surgery at least about 24–36 hours from the time of donation.

Figure 6:
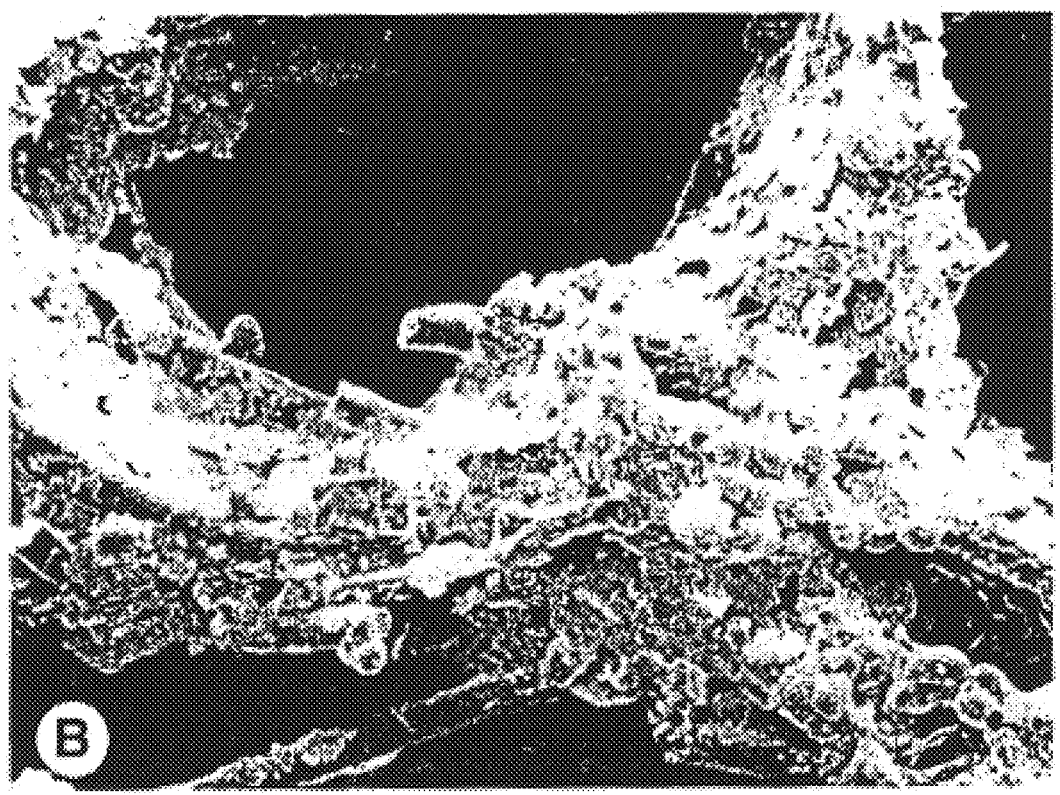

Most of the results presented here are from experiments using neonatal foreskin fibroblasts, as they are a convenient source of cells for experimental purposes. Neonatal foreskin fibroblasts are presently being used commercially, so these cells are readily available. We have, however, carried out experiments with dermal fibroblasts from a 78-year old donor and demonstrated that the procedure works as with neonatal fibroblasts, which shows there is no substantial age-dependence and that the methodology is not limited to neonatal fibroblasts. Thus Example 4 and FIG. 6 illustrate an embodiment in accordance with the invention where the original fibroblasts before conversion were isolated from 36 year old donor tissue.

In order to force conversion to chondrocyte phenotype, the fibroblast cells are first treated so as to modulate the redox state of the cells so as to place them in a state mimicking the effects of functional hypoxia (low oxygen tension). The fibroblasts, for example, may be placed in a state of hypoxia by incubating with a suitable hypoxia mimicking agent. Among the suitable hypoxia mimicking agents or conditions are lowered oxygen tensions ranging from between about 1.0%–7.5%, which can be used to create hypoxic culture conditions. Such methods have been used to stimulate chondrogenic differentiation in limb bud mesenchymal cells. In addition, oxygen free-radical scavengers (i.e. antioxidants) such as superoxide dismutase and N-acetyl-cysteine may be used for this purpose. Also, agents that regulate free AND (nicotinamide adenine dinucleotide) levels, such as 3-aminobenzamide, may also be effective in this capacity.

A preferred hypoxia mimicking agent is lactate, and we illustrate the first step of the invention by the use of lactate, preferably at concentrations in the range of about 10–40 mM. The action of lactic acid is believed to be mediated through its conversion to pyruvic acid by the enzyme lactate dehydrogenase. In this process, NAD is converted to NADH, reducing the pool of free NAD which can bind to and activate the enzyme polyADPribose (PADPR) synthetase. This enzyme is responsible for modifying nuclear proteins that regulate gene expression, presumably those which block chondrogenesis. By reducing the pool of NAD by the addition of NAD substrates like 3-aminobenzamide, the inhibitory activity of PADPR synthetase will be abrogated, allowing gene expression necessary for chondrogenesis to proceed.

In wound healing, lactate levels have been measured to be between 10–15 mM, and studies have shown that hyaluronan synthesis is increased in human dermal fibroblasts in the presence of 20 mM lactate. Although levels of sulfate incorporation peak at lactate concentrations of 20–40 mM (there were no statistically significant differences between these two concentrations), the cell cultures exhibit less fibroblast outgrowth from the micromass cultures when treated with 40 mnM lactate as compared to 20 mM lactate. As such, 40 mM lactate is the preferred dosage.

During the treating of cells so as to place them in a state mimicking the effects of functional hypoxia, the cells are preferably cultured as a high density micromass. By "high density micromass" is meant a cell culture technique which mimics the cellular condensation stage that occurs during the onset of cartilage formation in the developing limb. In this transient condensation phase, undifferentiated prechondrogenic mesenchymal cells migrate to a site and become closely juxtaposed, establishing crucial cell-cell interactions, prior to cartilage tissue formation.

A convenient means of culturing the cells as a high density micromass is to seed them onto three-dimensional biocompatible scaffolds. One such suitable scaffold is in the form of non-woven mesh, such as is commercially available from Davis and Geck, Danbury, Conn., and composed of polyglycolic acid, which we have further reinforced in a dilute solution of 100 kDa poly(L-lactic acid). However, other suitable means of culturing in a high density micromass is by use of polymer sponges as, for example sponges composed entirely of PLLA which possess a more refractile surface topography.

Figure 1:
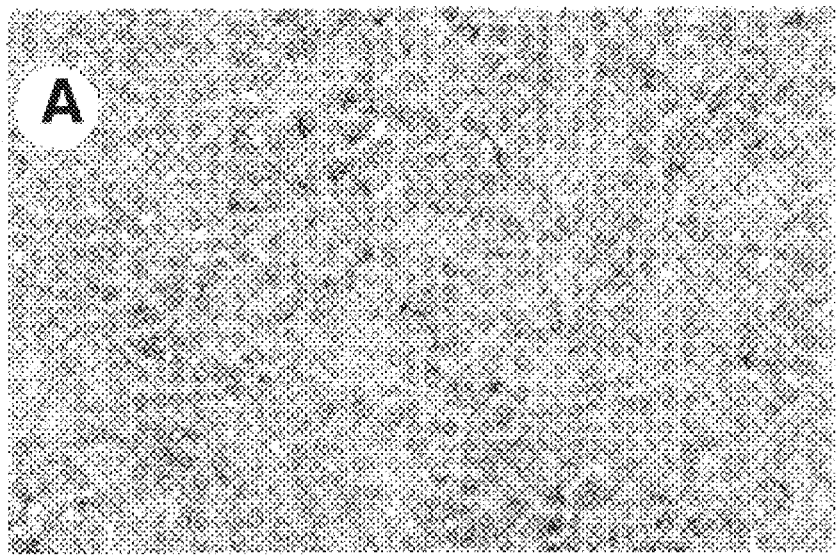
FIG. 1 illustrates the morphology of inventively treated micromass cultured cells, by inverted phase contrast microscopy.

Turning to FIG. 1, the morphology of inventively treated cells in micromass cultures at a density of $2 \times 10^5$ cells/ml (after 24 hours in the presence of 40 mM lactate and 200 nM staurosporine) is shown. The cells displayed a rounded, cobblestone-shaped morphology typical of chondrocytes. By contrast, cells that had been cultured only in the presence of lactate exhibited a more elongated morphology characteristic of fibroblast-like cells.

Figure 2:
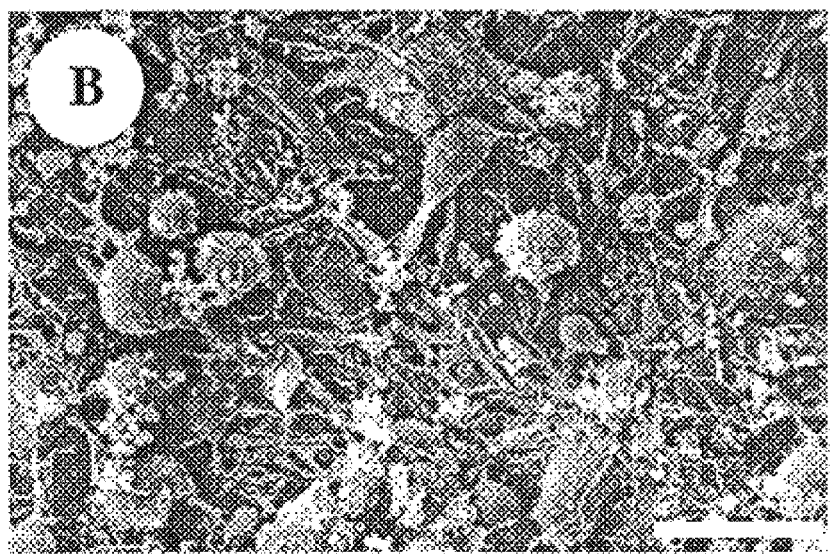
FIG. 2 is a scanning electron micrograph of inventively treated cells (magnification 1150 times, bar equals 20 μm) cultured on a three-dimensional polymer scaffold.

FIG. 2 is analogous to FIG. 1 but where the cells had been seeded in micromass culture onto a polymer scaffold. The cells are at a magnification of 115× and again exhibited a more rounded morphology resembling that of chondrocytes (as opposed to flattened layers of fibroblast-like cells in untreated controls).

Figure 3:
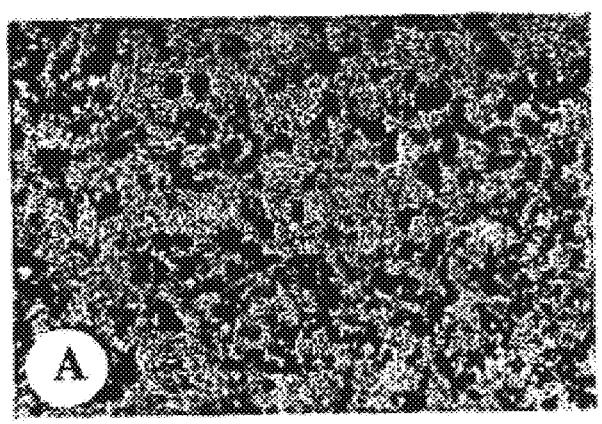
FIG. 3 is a light micrography image showing immunohistochemical detection of type II collagen in high density micromass cultures of inventively treated cells where, after conversion, the cultures were maintained in chemically defined medium for three days, then fixed and immunostained with a monoclonal antibody to type II collagen.

FIG. 3 shows the detection of type II collagen in high density micromass cultures of cells converted in accordance with the invention. Human foreskin fibroblasts had been seeded in micromass cultures at a density of $2 \times 10^5$ cells/ml and then converted by culturing over 24 hours with 40 mM lactate and 200 nM staurosporine, and then maintained in chemically defined medium for three days. The abundant, positively stained type II collagen was observed only in cultures treated with both lactate and staurosporine. Type II collagen is a characteristic of chondrocytes.

Figure 4:
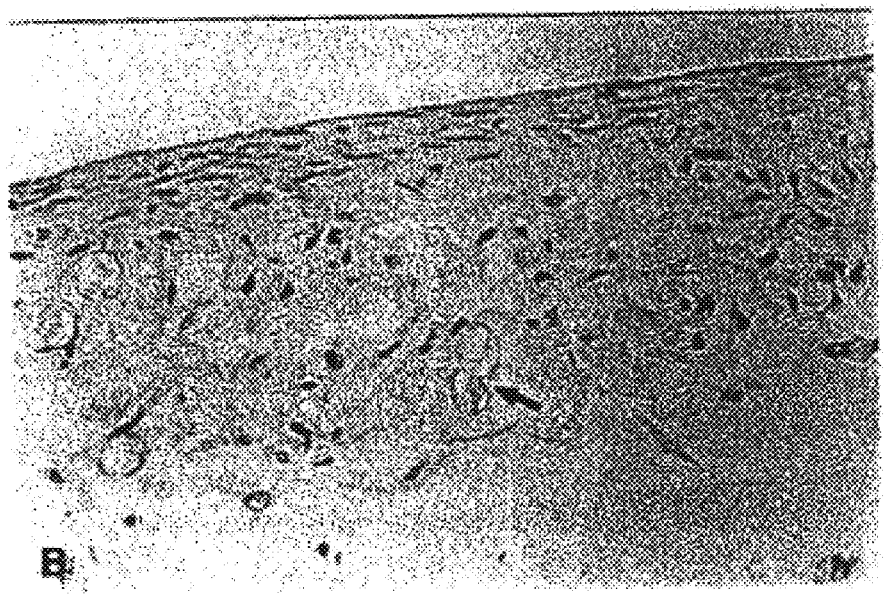
FIG. 4 is an enlarged view (magnification 200×) for histological evaluation of an inventive embodiment where the cells were cultured on a three-dimensional polymer scaffold and maintained 72 hours in culture.

FIG. 4 illustrates inventively treated cells on non-woven fiber scaffold after 72 hours in culture. The cellular organization is consistent with articular cartilage and has a surface layer containing spindle-shaped cells aligned parallel to the underlying substrate and a middle zone with polygonal-shaped cells in a random organization. By contrast, untreated controls showed dense layers of fibroblast-like cells. The magnification is 20× and the arrow denotes cross-sections of polymer fibers.

Figure 5:
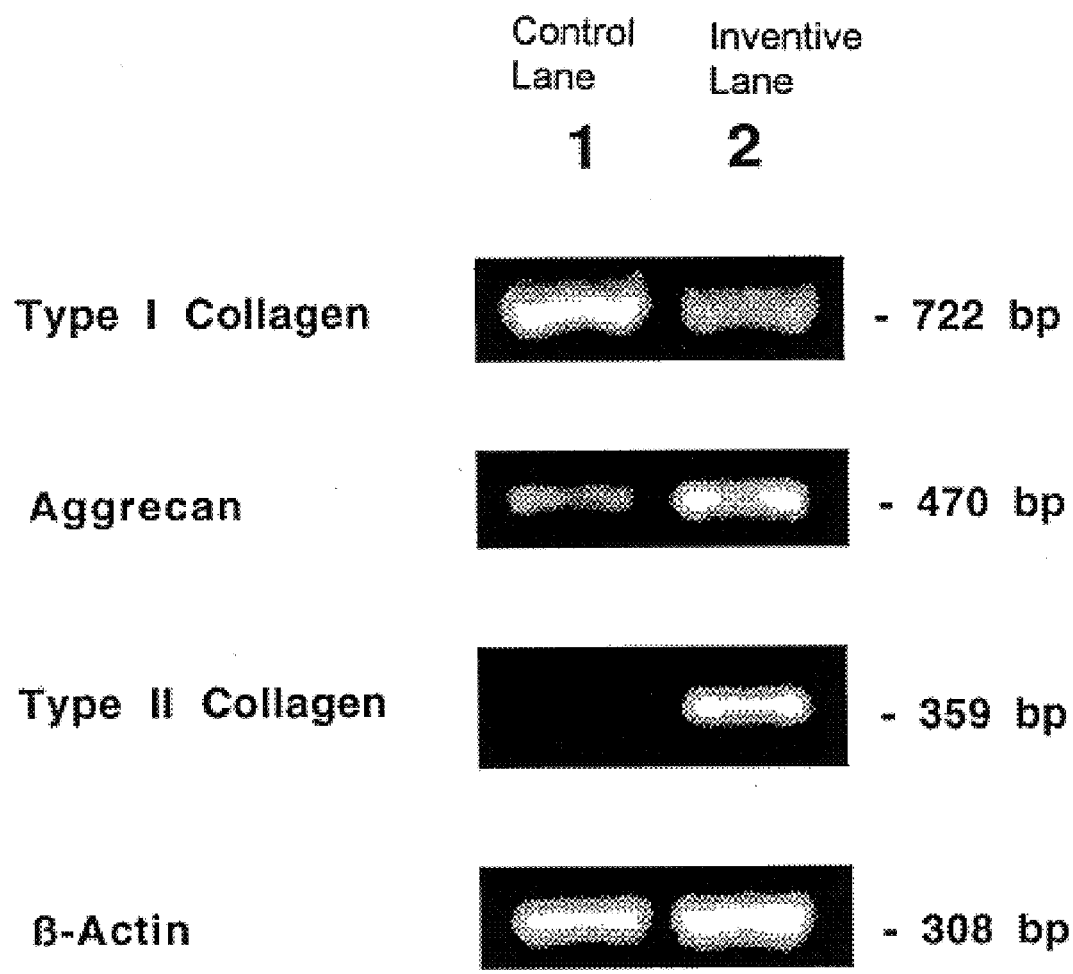
FIG. 5 illustrates photographs of gels in which a control lane 1 is shown alongside an inventive lane 2 for each of amplified type I collagen, aggrecan, type II collagen, and β-actin (which served as an internal standard); and, FIG. 6 is a scanning electron micrograph of cells treated in accordance with the invention on a three-dimensional polymer scaffold (magnification 600×).

FIG. 5 illustrates the results of mnRNA expression in cell-polymer constructs by RT-PCR. Neonatal foreskin fibroblasts were cultured at a density of $2.0 \times 10^5$ cells/ml on three-dimensional polymer scaffolds composed of a non-woven fiber mesh of polyglycolic acid (PGA) reinforced with 100 kDa poly(L-lactic acid). Cultures were untreated (lane 1) or treated with 40 mM lactic acid and 200 nM staurosporine (lane 2) for 24 hours, after which they were maintained in chemically defined medium. At three days, total cellular RNA was extracted using the Ultraspec isolation system (Biotecx Laboratories, Inc., Houston, Tex.) and subject to RT-PCR analysis employing the Superscript® Preamplification System for first strand cDNA synthesis (Life Technologies, Gibco BRL, Gaithersburg, Md.). Oligonucleotide primers used to amplify type II collagen and aggrecan were as published (Wagget et al., *Matrix Biology*, 16, pp.457–470, 1998) while those for β-actin and type I collagen were designed using computer-aided software based on the sequences of the respective genes. An increase in aggrecan and type II collagen mRNA expression and a concommitant decrease in type I collagen expression was observed in cultures treated in accordance with the invention (lane 2), in comparison to untreated controls (lane 1). β-actin served as an internal standard.

FIG. 6 is a scanning electron micrograph at a magnification of 600×. The inventively treated cells on a non-woven mesh scaffold have formed clusters displaying the rounded morphology typical of differentiated chondrocytes, and in contrast to flattened layers of fibroblasts-like cells that were observed in untreated controls.

The following experimental data of Examples 1 and 2 illustrate the initial steps in converting fibroblasts in accordance with this invention.

EXAMPLE 1

High Density Micromass Culture and Functional Hypoxia.

Experiments were designed to examine the effects of functional hypoxia and high density culture conditions on the phenotype of dermal fibroblasts. Human dermal fibroblasts obtained from neonatal foreskin samples were cultured in high density micromass cultures. Briefly, a 10 µl drop of a cell solution at a concentration of $2.0 \times 10^4$–$4.0 \times 10^4$ cells/µl was plated in a 24-well polystyrene tissue culture dish. The cultures were incubated for one hour at 37° C., 5% $CO_2$ to allow the cells to adhere to the bottom of the wells and to enhance cell:cell interactions. Following incubation, the cells were flooded with 1 ml of medium (bringing the final concentration to $2.0 \times 10^5$ to $4.0 \times 10^5$ cells/ml) containing exogenous factors that promote differentiation along the chondrogenic pathway. Cultures were made functionally hypoxic by the addition of lactate (10–40 mM) to the culture medium. The cells were cultured for a period of 24 hours.

Morphology. Gross examination of these cells indicated an irregular morphology, distinct from that of the fibroblast-like cells observed on the periphery of the micromasses, although not yet typical of chondrocytes.

Matrix Deposition. Treated micromass cultures synthesized highly negatively charged sulfated proteoglycan aggregates, as detected using histological and biochemical methods. At 24 hours, cells cultured at high cell density and in the presence of lactate stained more intensely with 1% Alcian blue dye (pH 1.0, in 0.1 N HCl) as compared to untreated monolayer, micromass, and treated monolayer cultures. Human dermal fibroblasts were seeded in monolayer or micromass cultures at a density of $2.0 \times 10^5$ cell/ml for 24 hours and left untreated or treated with 40 mM lactate to mimic the effects of functional hypoxia. Cultures were then fixed and stained overnight with 1.0% Alcian blue (pH 1.0 with 0.1 N HCl) to detect sulfated proteoglycan content in the extracellular matrix. The intensity of Alcian blue staining from guanidine-HCl extracts was measured using a microplate reader at a wavelength of 595 nm. High density micromass cultures in the presence of 40 mM lactate showed a significantly greater degree of staining (* $P<0.05$) than corresponding cell cultures.

Similarly, cultures metabolically labeled with [$^{35}$S]-sulfate showed relative levels of incorporation (normalized to [$^3$H]-thymidine) that were significantly greater than in controls. Thus, human dermal fibroblasts were seeded in monolayer or micromass cultures at a density of $2.0 \times 10^5$ cell/ml for 24 hours and left untreated or treated with 40 mM lactate to induce hypoxia. Cultures were labeled with [$^3$H]-thymidine at 2 µCi/ml and $Na_2^{35}SO_4$ at 5 µCi/ml 24 hours prior to harvest. Relative levels of [$^{35}$S]-sulfate uptake (ratio of [$^{35}$S]-sulfate to [$^3$H]-thymidine) were determined by liquid scintillation counting of soluble cell extracts using a dual label DPM counting program. Significantly greater levels of [$^{35}$S]-sulfate incorporation (* P<0.05) were observed in high density micromass cultures in the presence of 40 mM lactate as compared to corresponding cell cultures.

A dose-dependent increase in sulfate uptake was also observed in micromass cultures treated with lactate, peaking at concentrations of 20–40 mM. Human dermal fibroblasts were seeded in high density micromass cultures at a density of 2.0×10$^5$ cell/ml, treated with lactate at varying concentrations (0–80 mM) for a 24 hour period, and labeled with [$^{35}$S]-sulfate. A dose-dependent increase in sulfate uptake was observed in lactate-treated micromass cultures with relative values of incorporation peaking at 20–0 mM.

Finally, a cell density-dependent increase in sulfate incorporation was measured in hypoxic micromass cultures ranging in initial cell plating density of 50,000 cells/ml to 400,000 cells/ml.

Gene Expression. Enhanced synthesis of cartilaginous proteoglycan aggregates was also confirmed by northern hybridization of total cellular RNA using a DIG-labeled probe to aggrecan core protein. Expression of core protein was upregulated in micromass cultures treated with lactate in comparison to untreated monolayer, micromass, and treated monolayer cultures. The expression of TGF-β1 was also examined in cells cultured under identical conditions. Northern analysis confirmed that TGF-β1 was induced at greater levels than in control cultures. Human dermal fibroblasts were cultured in monolayer without or with 40 mM lactate or in micromass cultures without or with 40 mM lactate at a density of 3.0×10$^5$ cell/ml for 24 hours. Total cellular RNA extracted using the Ultraspec isolation system (Biotecx Laboratories, Inc., Houston, Tex.) and fractionated by formaldehyde-agarose gel electrophoresis was hybridized with DIG-labeled probes to human chondroitin sulfate proteoglycan (aggrecan) core protein and TGF-β1. An equal amount of RNA (5 μg) was loaded in each lane and 28s ribosomal RNA served as an internal control. A marked increase in both core protein and TGF-β1 gene expression was observed in lactate-treated micromass cultures.

Interestingly, type I collagen gene expression was reduced in similar lactate-treated micromass cultures. Human dermal fibroblasts were cultured in monolayer without or with 40 mM lactate or in micromass cultures without or with 40 mM lactate at a density of 2.0×10$^5$ cell/ml for 24 hours. Total cellular RNA extracted using the Ultraspec isolation system (Biotecx Laboratories, Inc., Houston, Tex.) and fractionated by formaldehyde-agarose gel electrophoresis was hybridized with a DIG-labeled probe to human type I collagen. An equal amount of RNA (5 μg) was loaded in each lane and 28s ribosomal RNA served as an internal control. A noticeable decrease in type I collagen gene expression was observed in lactate-treated micromass cultures.

In general, increased expression of TGF-β1 in dermal fibroblasts would be expected to enhance type I collagen synthesis. This unusual pattern of gene expression suggests a biphasic signaling cascade acting in lactate-treated micromass cultures, believed to favor chondrogenesis.

Practice of the invention further comprises contacting the cultured cells with at least one agent that promotes differentiation along the chondrogenic pathway. Thus, the fibroblasts are preferably cultured by substantially simultaneously incubating with the hypoxia mimicking agent and a chondrogenic pathway differentiation agent, such as by using an admixture of the two agents or else adding the two agents simultaneously at the time of plating.

The unique combination of compressive mechanical forces and low oxygen concentrations acting in developing cartilage has been known to induce cartilage formation ill vitro in chick embryonic mesenchymal cells. The signaling events that occur under these conditions are likely to involve cross-talk between secondary messengers such as protein kinases and cytokines. Specifically, protein kinase A (PKA) also referred to as cAMP-dependent protein kinase, is known to be required for the early stages of chick limb bud chondrogenesis. Cyclic AMP activators such as dibutyryl cyclic AMP (db-cAMP) enhance chondrongenesis through the action of PKA. Conversely, phorbol 12-myristate 13-acetate (TPA), a protein kinase C (PKC) activator, represses chondrogenic differentiation in limb bud mesenchymal cells, while inhibitors of PKC stimulate chondrogenic differentiation in similar limb bud cultures. This suggests the involvement of two opposing transduction pathways in chondrogenesis, a cAMP-PKA-dependent stimulatory cascade and a PKC-dependent inhibitory cascade.

Without being bound by theory, we believe that the cells treated as has been already described primes them for differentiation along the chondrogenic pathway. However, overt differentiation is believed blocked by a PKC-dependent antagonistic signal cascade.

Accordingly, practice of the invention includes treating the cells with the second agent so as to allow a PKA-dependent antagonistic pathway to predominate and to drive chondrogenic differentiation. Suitable chondrogenic differentiation agents include Bisindolylmaleimide I and calphostin C. PKA activators such as dibutyryl cAMP and adenylate cyclase activators (which results in cAMP production and PKA activity) like forskolin may also be effective. A preferred such agent is staurosporine (a protein kinase inhibitor to which PKC is most sensitive), preferably in a range of 150–200 nM. In concentrations of about 5–20 nM no visible effect was observed in lactate-treated micromass cultures. Treatment with the inhibitor staurosporine alone, without priming the cells as described by the lactate-induced functional hypoxic step, and even at otherwise effective doses, appears to have a deleterious effect on cell viability, as determined from direct microscopic observation and decreased levels of sulfate incorporation.

Chondrogenic differentiation along the pathway can be readily determined by conducting standardized tests for conversion to chondrocyte phenotypes, such as one or more characteristics: the cellular morphology, the production of cartilage matrix components detectable by histochemical procedures and metabolic labeling, the expression of aggrecan and type II collagen mRNA, and the down-regulation of type I collagen mRNA.

EXAMPLE 2

Human dermal fibroblasts were seeded in micromass cultures at a density of 2.0×10$^5$ cells/ml for 24 hours in the presence of 40 mM lactate and varying concentrations of the protein kinase C inhibitors, staurosporine (0, 50, 100, 150, and 200 nM in lanes 1–5, respectively). Total cellular RNA extracted using the Ultraspec isolation system (Biotecx Laboratories, Inc., Houston, Tex.) and fractionated by formaldehyde-agarose gel electrophoresis was hybridized with DIG-labeled probes to human chondroitin sulfate proteoglycan (aggrecan) core protein and type I collagen. An equal amount RNA (5 μg) was loaded in each lane and 28s ribosomal RNA served as an internal control. A notable increase in core protein gene expression was observed in lactate-treated micromass cultures supplemented with 150 nM (lane 4) and 200 nM (lane 5) staurosporine, while a marked decrease in type I collagen expression was evident in all cultures supplemented with staurosporine.

Turning to FIG. 1, human dermal fibroblasts that had been seeded in micromass cultures at a density of $2.0 \times 10^5$ cells/ml for 24 hours in the presence of 40 mM lactate with 200 nM staurosporine are shown. These inventively lactate-treated cell cultures supplemented with staurosporine displayed a rounded, cobblestone-shaped morphology typical of chondrocytes.

Turning to FIG. 2, human dermal fibroblasts that had been seeded in micromass cultures at a density of $2.0 \times 10^5$ cells/mi for 24 hours on PGA/PLLA matrices (PGA is polyglycolic acid and PLLA is poly (L-lactic acid)) with 40 mM lactate and 200 nM staurosporine as shown. The PGA non-woven mesh was obtained from Davis and Geck, Danbury, Conn., and then was reinforced in a dilute solution of 100 kDa PLLA, as described in *Clin. Plast. Surg.*, 21, pp. 442465 (1994). Cells cultured on PGA/PLLA scaffolds in the presence of lactate and staurosporine exhibited a more rounded morphology resembling that of chondrocytes.

As illustrated by Examples 1 and 2 above, we have successfully converted fibroblast cells into a chondrocyte phenotype, which conversion is typically accomplished by the treatments described over at least about 12 hours up to about 36 hours, most preferably in a time frame of about 16–24 hours. The cells are converted, or may be viewed as having been "primed;" however, it is important to maintain the chondrocyte phenotype prior to implantation for patients in need of cartilage repair.

The just described mesh scaffold could be adapted in size and shape for use in repairing cartilage. The three-dimensional polymer scaffold used as described above is intended to be illustrative of the wide variety of biomaterials (i.e. biocompatible materials) useful as scaffolds, or matrices, in tissue engineering applications. Among the matrix materials useful for filling or otherwise dressing defects in the cartilage are those including fibrinogen (activated with thrombin to form fibrin in the defect or lesion), collagen, Sepharose gel (available from Pharmacia), gelatin, and any other material, preferably biodegradable, which forms a matrix, preferably with pores sufficiently large to allow repair cells to populate and proliferate within the matrix and which can be degraded and replaced with cartilage during the repair process.

The matrices may be preformed or may be formed in situ, for example, by polymerizing compounds and compositions such as fibrinogen to form a fibrin matrix. Matrices that may be preformed include collagen (e.g., collagen sponges and collagen fleece), chemically modified collagen, gelatin beads or sponges, a gel-forming substance such as Sepharose gel, or other gel-forming or composite substances that are composed of a biodegradable matrix material to fill the defect and allow repair cells to populate the matrix, or mixtures of the above. For example, collagen gel can be overlaid onto a polyglycolic acid fiber matrix.

In a recent article appearing in *Biomaterials*, Vol. 17, Mizuno and Glowacki describe a three-dimensional composite of demineralized bone powder and collagen VI in vitro analysis of chondroinduction of human dermal fibroblasts, which was used to assess chondroblastic differentiation of human dermal fibroblasts. Although the authors showed that dermal fibroblast cultures in vitro on composites of DBM and collagen displayed a metachromatic matrix characteristic of cartilage, there was not further demonstration that the dermal fibroblast possessed chondrogenic differentiation potential. Nevertheless, the article illustrates another example of a suitable matrix with which the subject invention can be used by seeding fibroblast-derived cells.

However, the chondrogenic activity of the collagen-demineralized bone matrix (DMB) scaffold described by Mizuno et al. is likely due to soluble factors in the bone matrix such as bone morphogenetic proteins-2 and 4 (BMP-2, BMP-4) which have been reported to induce chondrogenesis in mesenchymal cells. Therefore, any material substrate containing such bioactive factors (i.e. BMP-2, BMP-4, TGF-β1) may be capable of stimulating chondrogenic differentiation in fibroblastic cells. An advantage of our inventive cell conversion or "priming" procedure is that it does not require the exogenous addition of these costly growth factors for promoting chondrogenesis in dermal fibroblasts.

The inventive cell conversion, or priming procedure, that has now been described leads to cells that can be promptly used for cartilage repair or the like treatment of bony defects. However, surgery for patients in need of such repairs (although typically voluntary and scheduled) may not be conveniently performed immediately. Thus, it will often be necessary or desirable to maintain the chondrogenic phenotype for one or two weeks prior to implantation. Although cells converted in accordance with the invention in a non-adhesive environment, can be kept substantially indefinitely, when these cells are seeded onto a scaffold, then we prefer to maintain them in a chemically defined, but serum-free media.

For example, a preferred such serum substitute is available from Gibco, Gaithersburg, Md., and includes insulin, transferrin, and selenium. Insulin assists in regulating glucose metabolism. Transferrin transfers iron in and out of the cells and assists in avoiding free radical formation, and selenium is a free radical scavenger. Other chemically defined, serum substitutes are available and known to the art.

Example 3 illustrates several other preparations in accordance with the invention, with the cells then maintained for seven days.

EXAMPLE 3

Human neonatal foreskin fibroblasts (HFFs) were cultured in high density micromasses ($2.0 \times 10^7$ cells/ml in 10 μl) and treated with 40 mM lactic acid and 200 nM staurosporine for a period of 24 hours as previously described by Examples 1 and 2. After the initial culture period, the cells were maintained in chemically defined medium consisting of minimum essential medium supplemented with a 1× mixture of Insulin-Transferrin-Selenium (Life Technologies, Gibco BRL, Gaithersburg, Md.), 4.5 g/l glucose, 10 mM β-glycerophosphate, and antibiotics. Dermal fibroblasts isolated from 36 year-old donor tissue were similarly cultured. Additionally, dermal fibroblasts were seeded on three-dimensional polymer scaffolds composed of a non-woven polyglycolic acid (PGA) (Davis and Geck, Danbury, Conn.) mesh reinforced in a dilute solution of 100 kDa poly(L-lactic acid) (PLLA) (Polysciences, Warrington, Pa.).

The production of sulfated proteoglycans was assessed by staining with 1% Alcian blue dye (pH 1.0), while monoclonal antibodies to collagen types I (Rockland, Gilbertsville, Pa.) and II (CIICl, Developmental Studies Hybridoma Bank, Iowa City, Iowa), aggrecan (Chemicon, Temecula, Calif.), and cartilage link protein (9/30/8-A-4, DSHB) were used for immuno-histochemical detection employing the Histostain-Plus king (Zymed, South San Francisco, Calif.) with a DAB substrate for final visualization. The expression of type I collagen and transforming growth factor-β1 (TGF-β1) was detected by northern hybridization. Cell-polymer composites were analyzed by scanning electron microscopy and were embedded in glycol methacrylate, sectioned, and stained with hematoxylin and eosin.

The HFFs cultured in high density micromasses in the presence of lactic acid and staurosporine displayed a rounded, cobblestone shaped morphology typical of differentiated chondrocytes and were organized into nodules which stained positively with Alcian blue. After three days, positive staining in a pattern similar to that observed with Alcian blue was seen in the whole mount cultures immunostained for aggrecan and cartilage link protein. Minimal staining was detected in untreated cultures or those treated only with lactate. Similarly, pericellular staining of type II collagen was detected only in cultures treated with lactate and staurosporine in comparison to corresponding controls (FIG. 3) Abundant staining for type I collagen was seen throughout untreated micromass cultures and only on the periphery of cultures treated with lactate alone, whereas virtually no staining was detected in cultures supplemented with both lactate and staurosporine.

HFFs were also cultured on PGA/PLLA discs (1 cm diameter, 1 mm thickness) in high density micromass cultures as described above in the presence of lactate and staurosporine. Histological analysis revealed a more rounded and polygonal cell shape at 24 hours in experimental constructs in comparison to the dense layers of fibroblast-like cells observed in untreated controls. These findings were confirmed by scanning electron microscopy. The expression of type I collagen was greater in untreated control cultures as compared to cultures treated with either lactate or with both lactate and staurosporine. Interestingly, TGF-β1 expression levels remained similar in all groups, suggesting that TGF-β1 may not be directly involved in differentiation along the chondrogenic pathway, or that the growth factor may be involved only in the very early prechondrogenic stages associated with cellular recruitment and migration. By three days, the cellular organization of the cell-polymer constructs treated with lactate and staurosporine resembled that of native articular cartilage with a surface (i.e. superficial) zone consisting of elongated cells aligned parallel to the underlying substrate, and a middle zone composed of more rounded, polygonal-shaped cells in a random orientation. In contrast, untreated control cultures of dermal fibroblasts seeded on PGA/PLLA scaffolds demonstrated extensive fibroblast outgrowth throughout the construct. Similar findings were also noted after seven days in culture on the PGA/PLLA scaffolds.

EXAMPLE 4

FIG. 5 illustrates the results of mRNA expression in cell-polymer constructs by RT-PCR. Neonatal foreskin fibroblasts were cultured at a density of $2.0 \times 10^5$ cells/ml on three-dimensional polymer scaffolds composed of a non-woven fiber mesh of polyglycolic acid (PGA) reinforced with 100 kDa poly(L-lactic acid). Cultures were untreated (lane 1) or treated with 40 mM lactic acid and 200 nM staurosporine (lane 2) for 24 hours, after which they were maintained in chemically defined medium. At three days, total cellular RNA was extracted using the Ultraspec isolation system (Biotecx Laboratories, Inc., Houston, Tex.) and subject to RT-PCR analysis employing the Superscript® Preamplification System for first strand cDNA synthesis (Life Technologies, Gibco BRL, Gaithersburg, Md.). Oligonucleotide primers used to amplify type II collagen and aggrecan were as published (Wagget et al., *Matrix Biology*, 16, pp. 457–470, 1998) while those for β-actin and type I collagen were designed using computer-aided software based on the sequences of the respective genes. An increase in aggrecan and type II collagen MRNA expression and a concomitant decrease in type I collagen expression was observed in cultures treated in accordance with the invention (lane 2), in comparison to untreated controls (lane I). β-actin served as an internal standard.

These so treated fibroblasts were isolated from 36 year old donor tissue. When seeded in high density micromasses and treated with lactate and staurosporine, 36 year old dermal fibroblast cultures displayed a rounded morphology similar to that observed with HFFs, and formed Alcian blue staining nodules. Also, positive staining for type II collagen and aggrecan was detected only in those cultures treated with lactate and staurosporine. Finally, cell-polymer composites of 36 year old dermal fibroblasts seeded on PGA/PLLA scaffolds treated with lactate and staurosporine formed clusters of rounded, polygonal cells whereas sheets of fibroblast-like cells were seen in controls (FIG. 6).

It is to be understood that while the invention has been described above in conjunction with preferred specific embodiments, the description and examples are intended to illustrate and not limit the scope of the invention.

We claim:

1. A method for producing cells with a chondrocyte phenotype, useful for autogenous tissue repair, comprising:
   obtaining fibroblasts derived from the dermis of an intended patient; and
   culturing the fibroblasts in a state of hypoxia and in the presence of at least one agent that promotes differentiation along a chondrogenic pathway;
   wherein said culturing provides for conversion of the fibroblasts to display a chondrocyte phenotype even in the absence of exogenously added growth factor, the chondrocyte phenotype being selected from the group consisting of production of type II collagen with down-regulation of type I collagen, expression of aggrecan and type II collagen mRNA with down-regulation of type I collagen, chrondrocyte cellular morphology, and production of at least one cartilage matrix component.

2. The method of claim 1, further comprising transplanting the fibroblasts displaying a chondrocyte phenotype into the intended patient.

3. The method of claim 1, wherein said culturing comprises exposing the fibroblasts to lactate.

4. The method as in claim 1 wherein the culturing includes exposing the cells to staurosporine.

5. The method as in claim 1, wherein the fibroblasts are obtained from dermal cells.

6. A cartilage repair composition, comprising:
   a matrix; and,
   cells displaying a chondrocyte phenotype seeded on the matrix, the cells being derived from non-chondrocytes cultured in a state of hypoxia and in the presence of at least one agent that promotes differentiation along a chondrogenic pathway even in the absence of exogenously added growth factors.

7. The cartilage repair composition of claim 6, wherein the matrix is a biodegradable matrix.

8. A tissue repair composition, comprising:
   a high density micromass of non-chondrocyte cells in a synthetic media, wherein the non-chondrocyte cells are in a state of hypoxia and the media includes at least one agent that promotes differentiation along a chondrogenic pathway, said state of hypoxia and said agent producing a chondrocyte phenotype in the non-chondrocyte cells even in the absence of exogenously added growth factors.

9. An isolated cell culture composition, comprising:

non-chondrocyte cells displaying a chondrocyte phenotype in a cell culture medium, the cell culture medium comprising a hypoxia-inducing agent and at least one agent which promotes differentiation along a chondrogenic pathway even in the absence of exogenously added growth factors.

10. The isolated cell culture composition of claim 9, wherein the non-chondrocyte cells are fibroblast cells.

11. The isolated cell culture composition of claim 10, wherein the chondrocyte phenotype is a phenotype selected from the group consisting of production of type II collagen with down-regulation of type I collagen, the expression of aggrecan and type II collagen mRNA with down-regulation of type I collagen, chrondrocyte cellular morphology; and the production of at least one cartilage matrix component.

12. The isolated cell culture composition of claim 10, wherein the hypoxia-inducing agent comprises lactate.

13. The isolated cell culture composition of claim 10, wherein the agent which promotes differentiation along a chondrogenic pathway is a PKC inhibitor.

14. The isolated cell culture composition of claim 13, where the PKC inhibitor is staurosporine.

* * * * *